(12) United States Patent
Na et al.

(10) Patent No.: US 9,029,334 B2
(45) Date of Patent: May 12, 2015

(54) PHARMACEUTICAL COMPOSITION FOR PREVENTION OR TREATMENT OF BONE DISEASES COMPRISING SPINASTEROL GLUCOSIDE DERIVATIVE

(71) Applicant: Lifetree Biotech Co., Ltd., Suwon-si (KR)

(72) Inventors: Chun-Soo Na, Suwon-si (KR); Cheol Yi Hong, Suwon-si (KR); Hee Kyong Kim, Gwangju-si (KR); Sun-Young Yoon, Gunpo-si (KR); Jin-Beom Kim, Ansan-si (KR); Hyun-Jung Roh, Yongin-si (KR); Hye-Ji Noh, Ulsan (KR); Na-Na Um, Suwon-si (KR); Jiyoung Kim, Seoul (KR); Tae Hoon Lee, Suwon-si (KR)

(73) Assignee: Lifetree Biotech Co., Ltd., Suwon-Si (KR)

( * ) Notice: Subject to any disclaimer, the term of this patent is extended or adjusted under 35 U.S.C. 154(b) by 0 days.

(21) Appl. No.: 13/893,240

(22) Filed: May 13, 2013

(65) Prior Publication Data
US 2014/0296170 A1    Oct. 2, 2014

(30) Foreign Application Priority Data

Mar. 29, 2013 (KR) .......................... 10-2013-0034395

(51) Int. Cl.
*A61K 31/70* (2006.01)
*A61K 31/704* (2006.01)

(52) U.S. Cl.
CPC .................................... *A61K 31/704* (2013.01)

(58) Field of Classification Search
CPC .............................. C07H 15/24; A61K 31/704
See application file for complete search history.

(56) References Cited

U.S. PATENT DOCUMENTS

| | | |
|---|---|---|
| 2005/0197353 A1 | 9/2005 | Ritzeler et al. |
| 2007/0244139 A1 | 10/2007 | Ritzeler et al. |
| 2010/0028463 A1* | 2/2010 | Kim et al. ................. 424/725 |

FOREIGN PATENT DOCUMENTS

| | | |
|---|---|---|
| JP | 2012-527484 A | 11/2012 |
| KR | 10-2005-7002707 A1 | 6/2005 |
| KR | 10-2007-0002715 A1 | 1/2007 |
| KR | 10-2008-0065722 A | 7/2008 |
| KR | 10-1162046 B1 | 7/2012 |
| WO | 2004/022553 A1 | 3/2004 |
| WO | 2010/135703 A2 | 11/2010 |

OTHER PUBLICATIONS

Grynkiewicz et al., "Synthetic analogs of natural glycosides in drug discovery and development," *Acta Poloniac Pharmaceutica—Drug Research* 65(6):655-676, 2008.

Jung et al., "Suppression of thymus- and activation-regulated chemokine (TARC/CCL17) production by 3-$O$-$\beta$-D-glucopyanosylspinasterol via blocking NF-κB and STAT1 signaling pathways in TNF-$\alpha$ and IFN-$\gamma$-induced HaCaT Keratinocytes," *Biochemical and Biophysical research Communications*, 2012, 6 pages.

Lee et al., "inhibitory effects of a spinasterol glycoside on lipopolysaccharide-induced production of nitric oxide and proinflammatory cytokines via down-regulating MAP kinase pathways and NF-κB activation in RAW264.7 marcophage cells," *International Immunopharmacology* 13:264-270, 2012.

* cited by examiner

*Primary Examiner* — Elli Peselev
(74) *Attorney, Agent, or Firm* — Seed IP Law Group PLLC

(57) ABSTRACT

Disclosed is a pharmaceutical composition for the prevention or treatment of metabolic bone diseases, comprising a spinasterol glucoside derivative, or an optical isomer, a pharmaceutically acceptable salt, a hydrate or a solvate thereof. The pharmaceutical composition is effectively useful for preventing or treating metabolic bone diseases.

6 Claims, 2 Drawing Sheets

(a) Normal group (b) Control group (c) Spinasterol glucoside derivative-treated group

PHARMACEUTICAL COMPOSITION FOR PREVENTION OR TREATMENT OF BONE DISEASES COMPRISING SPINASTEROL GLUCOSIDE DERIVATIVE

TECHNICAL FIELD

The present invention relates to a pharmaceutical composition for the prevention or treatment of bone diseases, comprising a spinasterol glucoside derivative, an optical isomer thereof, a pharmaceutically acceptable salt thereof, a hydrate or a solvate thereof.

BACKGROUND ART

Among metabolic bone diseases are osteoporosis, osteomalacia, osteopenia, bone atrophy, fibrous dysplasia, Paget's disease, hypercalcemia, neoplastic destruction, cancer-related bone resorption, osteolysis, osteoarthritis, and rheumatoid arthritis.

Osteoporosis, the most common metabolic bone disease, occurs as a balance between osteoclastic bone resorption and osteoblastic bone formation is broken and is defined as a skeletal disorder characterized by compromised bone strength predisposing to an increased risk of fracture (The National Institutes of Health (NIH), 2000), indicating that osteoporosis is a kind of systemic diseases which leads to an increase risk of fracture across the body because the bone density is reduced and bone microarchitecture is disrupted. The bone density is homeostatically maintained through the exhaustion of old bones and the formation of new bones. This bone replacement is reduced with age, causing bone loss. Continuous repetition of this imbalance state causes the bone to become thin, increasing the rise of bone fracture and destruction. There are two factors that affect bone density: bone mineral density and bone quality. Bone quality is a composite of properties that make bones resist fracture, such as its microarchitecture, bone turnover, mineral crystal size, accumulated microscopic damage, quality of collagen, etc. Patients with osteoporosis are likely to undergo bone fracture even upon a light impact because their bone calcium level and bone mass, that is, bone density, are significantly reduced. Therefore, patients with osteoporosis are restrained from doing physical activities in daily life.

Osteopenia may be considered to be a precursor to osteoporosis, and is a condition wherein the bone becomes thinner and lighter before development of pores.

Osteomalacia is the softening or bending of the bones caused by a deficiency of vitamin D or excessive loss of calcium, particularly in patients with renal diseases. Bone atrophy is a degenerative decrease in bone mass, that is, a reduction of the bone mass of preexisting bone tissue.

Rheumatoid arthritis is an autoimmune disease that strikes women in their thirties to fifties about four times as often as men. Rheumatoid arthritis typically manifests with signs of symmetrical inflammation around joints such as finger joints, elbow joints, knee joints, etc., with the affected joints becoming swollen, painful and stiff, particularly early in the morning on waking. It is often accompanied by mild fever. Symptoms of rheumatoid arthritis, while disappearing within days to weeks if it is acute, last for months to years, causing deformation and dislocation of joints, and contracture and stiffness of muscles and tendons, thus leading to disability.

Osteoarthritis is a disease which is caused by a local degenerative change in articular cartilage. Osteoarthritis is a chronic degenerative disorder related to aging, affecting 10~15% of the population. It is estimated that 60~80% of the population have evidence of osteoarthritis by the age of 65.

In addition, renal osteodystrophy, a bone disease induced by renal failure, adynamic bone disease, which is increasing in prevalence in many chronic kidney disease populations, and infectious bone disease, caused by infection by pyogenic bacteria, are regarded as metabolic bone diseases.

The onset of such metabolic bone diseases is accounted for by an imbalance in activity between osteoblasts and osteoclasts which are responsible for the formation and removal of bone tissues, respectively. Osteoclasts are large cells with multiple nuclei, and function to break up and absorb unnecessary bone tissues during the metabolism of the bone. Mature osteoclasts are multinucleated, originated from hematopoietic stem cells. After differentiation from mesenchymal stem cells, osteoblasts survive for about 34 months. They form new bones at the site where activated osteoclasts break up old bones. A number of osteoblasts produce a matrix of osteoid and mineralize the matrix, accomplishing bone formation. After then, approximately 70% of osteoblasts die while some osteoblasts differentiate into osteocytes and bone lining cells. Since the quantity of bone is maintained by balanced activities of osteoclasts and osteoblasts, it is important to develop a therapeutic agent targeting molecules which exerts significant influence on osteoclastic activity. Given an increased activity, osteoclasts responsible mainly for bone resorption accelerate the degradation of bones, causing osteoporosis characteristics of bone thinning and bone fracture. Therefore, studies have been focused on proteins regulatory of osteoclastic activity as targets for the therapy of bone diseases (Gregory R. Mundy, Journal of Bone and Mineral Metabolism (1996) 14: 59-64; Chad Deal, nature clinical practice RHEUMATOLOGY (2009) vol 5 no 1; Kalervo Vaananen, Advanced Drug Delivery Reviews 57 (2005) 959-971).

Current clinical treatment of metabolic bone diseases resorts mostly to drugs (analgesics, steroidal agents, non-steroidal anti-inflammatory agents), cartilage protectants (hyaluronic acid, glycosamine, chondroitin, etc.), or surgical operation (anthroscopic surgery, wedge high tibial osteotomy, partial arthroplasty, total knee arthroplasty, etc.). However, the drugs non-specifically only relieve pain or inflammation itself, and cartilage protectants perform the protection of the joint simply by providing nutrients for chondrocytes or by absorbing a shock to the joint. Steroids, when used for a long term, induce calcium deficiency, which leads to the onset of osteoporosis, hypertension, and diabetes. Therefore, drugs are applied, for the most part, only for pain relief, and anthroplasty is mainly used for permanent purposes, but neither drugs nor surgical operations have been regarded as fundamental cures for metabolic bone diseases. In recent years, herbal medicaments and nutrients have been suggested as therapeutics for arthritis, but much must be done to demonstrate their therapeutic effects and mechanisms. Anti-inflammatory analgesics, simple symptomatic agents, cause significant side effects after long-term use, in addition to being unable to effectively regulate arthritis. There has been much difficulty in treating patients, especially the elderly.

Because, on the whole, therapeutic drugs for arthritis are required to be administered for a long term, there is a need for the development of a drug with fewer side effects.

PRIOR ART DOCUMENT

Patent Document

KR 10-2007-0002715, 2007 Jan. 10
KR 10-2005-7002707, 2005 Feb. 17

DISCLOSURE

Technical Problem

It is an object of the present invention to provide a pharmaceutical composition for the prevention or treatment of metabolic bone diseases which exhibits great pharmaceutical efficacy with fewer side effects.

Technical Solution

In accordance with an aspect thereof, the present invention provide a pharmaceutical composition for the prevention or treatment of metabolic bone diseases, comprising a spinasterol glucoside derivative represented by the following Chemical Formula 1, or an optical isomer, a pharmaceutically acceptable salt, a hydrate or a solvate thereof:

[Chemical Formula 1]

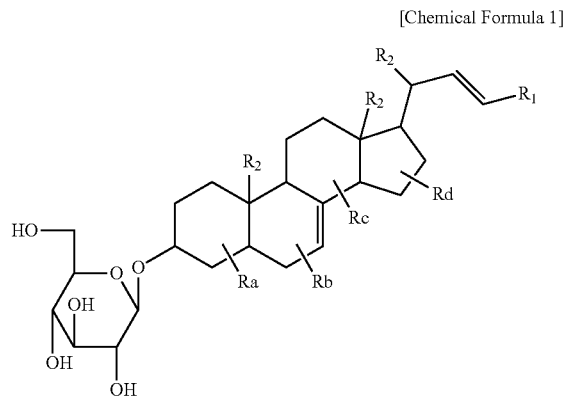

wherein,
- $R_1$ to $R_4$ may be the same or different, and are independently —H or a linear or branched alkyl of $C_1$ to $C_8$, and preferably a linear or branched alkyl of $C_1$ to $C_6$, and
- $R_a$ to $R_d$ may be the same or different, and are independently —H, or a linear or branched alkyl of $C_1$ to $C_4$.

The compound represented by Chemical Formula 1 may contain a chiral center. In this context, the present invention may comprise not only the compound represented by Chemical Formula 1, but also an optical isomer thereof.

In one preferred embodiment of the present invention, the spinasterol glucoside derivative represented by Chemical Formula may be a compound represented by the following Chemical Formula 2:

[Chemical Formula 2]

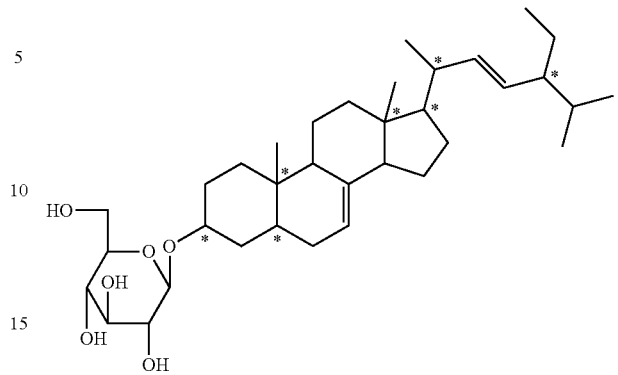

wherein * represents a chiral carbon atom.

Thus, the present invention includes the compound represented by Chemical Formula 2, an optical isomer thereof, a pharmaceutically acceptable salt thereof, a hydrate or a solvate thereof.

In another preferred embodiment of the present invention, the spinasterol glucoside derivative represented by Chemical Formula 1 may be a compound represented by the following Chemical Formula 3.

[Chemical Formula 3]

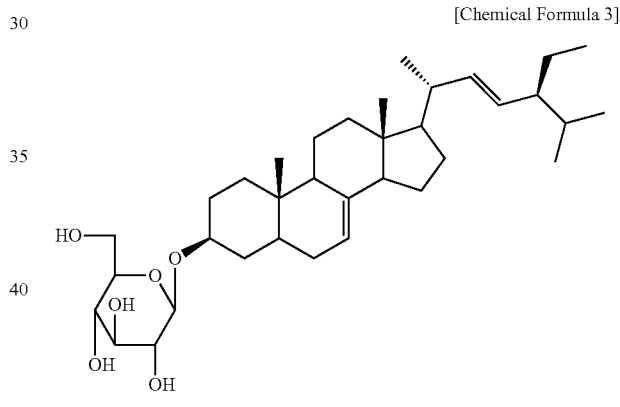

Hence, the compound represented by Chemical Formula 3, a pharmaceutically acceptable salt thereof, a hydrate or a solvate thereof fall within the range of the present invention.

Spinasterol glucoside derivatives represented by Chemical Formulas 1 to 3 may be separated from a *Stewartia koreana* extract or may be synthesized using a method well known in the art.

In the former case, for example, a methanol extract of *Stewartia koreana* is obtained by exuding ingredients in leaves of *Stewartia koreana* into methanol, and concentrating it by the depletion of the methanol. The concentrate is washed with hexane and ethyl acetate, and then dissolved in methanol. The methanol fraction is subjected to silica gel column chromatography and TLC to afford the compound.

The compound of the present invention has at least one chiral center, and thus may be in the form of an enantiomer. When the compound has two or more chiral centers, it may exist as a diastereomer as well.

It is apparent to those skilled in the art that such isomers and their racemates fall within the scope of present invention.

In the present invention the salts of the compounds of Chemical Formulas 1 to 3 may be any of pharmaceutically or physiologically acceptable salts. Examples of the salts include, but are not limited to, inorganic ion salts, such as salts of calcium, potassium, sodium and magnesium, inorganic acid salts, such as salts of hydrochloric acid, phosphoric acid, bromic acid, iodic acid, perchloric acid, stannic acid, and sulfuric acid, organic acid salts such as salts of acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galaturonic acid, glutamic acid, glutaric acid, glucuronic acid, aspartic acid, ascorbic acid, carbonic acid, vanillic acid, hydroiodic acid, mandelic acid, mucic acid, nitric acid, pamoic acid, pantothenic acid, succinic acid, and tartaric acid, and sulfonic acid salts, such as salts of methane sulfonic acid, ethane sulfonic acid, benzene sulfonic acid, p-toluene sulfonic acid, camphoric acid, and naphthalene sulfonic acid, amino acid salts such as salts of glycine, arginine, and lysine, and amine salts, such as salts of triethyl amine, triethylamine, ammonia, pyridine, and picoline. Salts of hydrochloric acid and methane sulfonic acid are representative of salts of inorganic and organic acids, respectively, which may be used as the pharmaceutically acceptable salts of the present invention.

A hydrate of the compounds of Chemical Formulas 1 to 3, the optical isomers or the pharmaceutically acceptable salts may comprise a stoichiometric or non-stoichiometric amount of water bound by non-covalent intermolecular forces.

The hydrate may comprise at least one equivalent of water, for example, one to five equivalents of water. It may be prepared by crystallizing the compounds, optical isomers thereof, or pharmaceutically acceptable salts thereof in water or an aqueous solvent.

A solvate of the compounds of Chemical Formulas 1 to 3, the optical isomers or the pharmaceutically acceptable salts may comprise a stoichiometric or non-stoichiometric amount of a solvent bound by non-covalent intermolecular forces. Preferred is a solvent which is non-volatile, non-toxic, and suitable for administration to humans. Ethanol, methanol, propanol, and methylene chloride may be exemplary.

Also, prodrugs of the compounds of Chemical Formulas 1 to 3 fall within the scope of the present invention. Generally, a prodrug is a medication that is administered as an inactive chemical derivative that is subsequently converted to an active pharmacological agent in the body. Therefore, the term "prodrug," as used in the context with the prevention and treatment of metabolic bone diseases in accordance with the present invention, in intended to refer to a compound that undergoes biotransformation into one of the compounds of Chemical Formulas 1 to 3 after it is administered. With regard to the selection and preparation of suitable prodrugs, reference may be made to, for example, "Design of Prodrugs", ed. H. Bundgaard, Elsevier, 1985. In addition, the compounds of the present invention, salts thereof, or isomers thereof may be in crystalline forms. Further, some of the compounds of the present invention may be associated with water of crystallization (that is, hydrates) or may form solvates with typical organic solvents. Hence, the present invention also envisages the hydrates and the solvates.

As described above, the compounds of Chemical Formulas 1 to 3 in accordance with the present invention exhibits prophylactic and therapeutic effects on metabolic bone diseases.

For example, the compounds of Chemical Formulas 1 to 3 are suppressive of weight loss, inflammation, edema, and stiffness of muscles and tendons, and regenerate the cartilage at worn joints, thus exhibiting prophylactic and therapeutic effects on metabolic bone diseases.

As used herein, the term "metabolic bone disease" is intended to include osteoporosis, osteomalacia, osteopenia, bone atrophy, fibrous dysplasia, Paget's disease, hypercalcemia, neoplastic destruction, cancer-related bone resorption, osteolysis, osteoarthritis, rheumatoid arthritis, and a metabolic syndrome or disease due to the concurrent onset thereof.

For proper administration, the pharmaceutical composition of the present invention may comprise at least one pharmaceutically acceptable carrier in addition to the compound of Chemical Formula 1 to 3, or an optical isomer, a pharmaceutically acceptable salt, a hydrate or a solvate thereof. The pharmaceutically acceptable carrier may include saline, sterile water, Ringer's solution, buffered saline, dextrose solution, maltodextrin solution, glycerol, ethanol, or a combination thereof. If necessary, the pharmaceutical composition may further comprise a typical additive such as an antioxidant, buffer, a bacteriostat, etc.

According to purpose, the pharmaceutical composition of the present invention may be administered orally or parenterally (e.g., intravenously, subcutaneously, intradermally, or topically). The therapeutically effective amount of the active ingredient may vary depending on various factors including patient's age, weight, gender, health condition, gender, and diet, the time of administration, the route of administration, the rate of excretion, constitutional disposition, the property of an agent to be administered, the severity of disease. The compounds of Chemical Formulas 1 to 3, optical isomers thereof, pharmaceutically acceptable salts thereof, hydrates or solvates thereof may be administered in an amount of from 0.01 to 100 mg/kg, and preferably in an amount of from 0.1 to 30 mg/kg once a day, or may be divided in triple doses a day.

For administration, the composition of the present invention may be formulated together with a pharmaceutically acceptable carrier into various pharmaceutical dosage forms. The carrier is a non-toxic and inert formulation auxiliary agent that may be in any phase, such as a solid, quasi-solid, or liquid phase. For example, a filler, a thickener, a binder, a wetting agent, a disintegrant, a dispersant, a surfactant, or a diluent may be employed.

The pharmaceutical composition of the present invention may be prepared into unit dosage forms. In the unit dosage forms, the compounds of Chemical Formulas 1 to 3, or optical isomers, pharmaceutically acceptable salts, hydrates or solvates thereof may be present in an amount corresponding to a fraction or a multiple of the daily dose thereof. For example, the unit dosage form may contain the active ingredient in an amount 1, 2, 3 or 4, or ½, ⅓ or ¼ times as much as a necessary daily dose thereof. Preferably, the amount of the active ingredient in a unit dosage form is a single dose which typically corresponds to ½, ⅓ or ¼ of the daily dose.

The pharmaceutical composition of the present invention may be formulated into a tablet, a coated tablet, a capsule, a pill, a granule, a suppository, a liquid, a suspension, an emulsion, a paste, an ointment, a gel, a cream, a lotion, a powder, or a spray. For oral administration, for example, the pharmaceutical composition of the present invention may be formulated into a solid agent such as a tablet, a pill, a powder, a granule or a capsule, or a liquid agent such a suspension, an internal use liquid, an emulsion or a syrup. Alternatively, the pharmaceutical composition of the present invention may be administered via a parenteral route. For this, the pharmaceutical composition of the present invention may be in the form of an injection, a suspension, an emulsion, a lyophilizate, or a suppository. For example, the compound of Chemical Formula, or an optical isomer, a pharmaceutically acceptable salt thereof, a hydrate or a solvate thereof may be formulated together with at least one excipient into a microcapsule.

When the pharmaceutical composition of the present invention is formulated into a solid preparation such as a tablet, a coated tablet, a capsule, a pill or a granule, the active ingredient may be combined with (a) a filter and a binder, such as starch, lactose, sucrose, glucose, mannitol, or silicate, (b) a binder, such as carboxymethyl cellulose, alginate, gelatin, polyethylene glycol, microcrystalline cellulose, highly dispersible silica, natural gum, synthetic gum, povidone, copovidone, polyvinyl pyrrolidone, or gelatin, (c) a moisture absorbent such as glycerol, (d) a disintegrant such as agar, calcium carbonate, or sodium carbonate, (e) a dissolution retardant such as paraffin, (f) an absorption accelerator such as a quaternary ammonium compound, (g) a humectant such as cetyl alcohol, or glycerol monostearate, (h) an absorber such as kaolin or bentonite, or (i) a lubricant such as talc, calcium stearate, magnesium stearate, or a solid polyethylene glycol, or a mixture of (a) to (i).

For formulating the pharmaceutical composition of the present invention into a liquid agent for oral administration, such as a suspension, an internal use liquid, or a syrup, various additives including a diluent such as water, liquid paraffin, etc., a humectants, a sweetener, an aromatic, a preservative, and a colorant may be necessary. For example, peppermint oil, eucalyptus oil or a sweetener such as saccharin may be added to the pharmaceutical composition of the present invention.

When the pharmaceutical composition of the present invention may be formulated into a suppository, a water-soluble or insoluble excipient such as a lipid, e.g., polyethylene glycol, cacao lipid, etc., a high ester (e.g., C14-alcohol with C16-fatty acid), Witepsol, macrogol, Tween 61, laurin butter, glycerol gelatin, or a combination thereof may be employed.

Also, the pharmaceutical composition of the present invention may take the form of ointments, pastes, creams or gels. In this regard, animal or vegetable lipids, wax paraffins, starch, tragacanth, cellulose derivatives, polyethylene glycol, silicon, bentonite, silicic acid, talc, zinc oxide or a combination thereof may be used.

For a powder or spray, the pharmaceutical composition of the present invention may be formulated in combination with lactose, talc, silicic acid, aluminum hydroxide, calcium silicate, polyamide powder, or a mixture thereof. Particularly, a spray formulation may further comprise a typical propellant such as chlorofluorohydrocarbon. PEG-4000 and glycerin are typically needed to obtain an inhalation spray.

As concerns liquid or emulsion formulations intended for the parenteral administration of the pharmaceutical composition of the present invention, they can be formulated with a solvent, a dissolving agent, or an emulsifier. For example, water, ethyl alcohol, isopropyl alcohol, ethyl carbonate, ethyl acetate, benzyl alcohol, benzyl benzoate, propylene glycol, 1,3-butylene glycol, dimethyl formamide, an oil such as cotton seed oil, peanut oil, corn seed oil, olive oil, castor oil, or sesame oil, glycerol, glycerol formalcohol, tetrahydrofurfuryl alcohol, polyethylene glycol, polyethylene glycol, a fatty acid of sorbitan, or a combination thereof may be used to formulate the composition of the present invention may be formulated into a liquid or an emulsion. The liquid or emulsion for parenteral administration may be sterilized and isotonic to the blood.

For use in formulating the pharmaceutical composition into a suspension, a liquid diluent, such as water, ethyl alcohol, propylene glycol, or polyethylene glycol, ethoxylated isostearyl alcohol, polyoxyethylene sorbitol, and sorbitan ester, microcrystalline cellulose, aluminum metahydroxide, bentonite, agar, tragacanth, an injectable ester such as ethyl oleate, and a mixture thereof may be suitable.

In addition, the pharmaceutical composition of the present invention may be formulated into a sustained or immediate release form with the aid of an excipient, a diluent, a dispersant, a surfactant, a binder, a lubricant and an additive. For example, the formulation may be intended to release the compounds of Chemical Formulas 1 to 3, or optical isomers, pharmaceutically acceptable salts thereof, hydrates or solvates thereof at a desired site of the body.

When the pharmaceutical composition of the present invention is formulated into a sustained release agent, an embedding agent, such as enteric coating agent, a water-insoluble polymer, a hydrophobic compound or a polymeric material such as a hydrophilic polymer, or wax may be employed. For example, when the pharmaceutical composition takes a form of tablets, capsules, pills or granules, a coating film may be applied to them to achieve a sustained release.

No particular limitations are imparted to the amount of the additives used in preparing a formulation of the pharmaceutical composition of the present invention, such as carriers, fillers, thickeners, binders, humectants, disintegrants, dispersants, surfactants, or diluents. It may be suitably adjusted within the range typically used in typical formulations.

Using a suitable method known in the art, the pharmaceutical composition of the present invention may be formulated depending on the disease to be treated or the ingredient to be used. For example, the compounds of Chemical Formulas 1 to 3, or optical isomers or pharmaceutically acceptable salts thereof may be formulated in mixture of an excipient into a desired preparation.

In the pharmaceutical composition of the present invention, the active ingredient, such as compounds of Chemical Formulas 1 to 3, or optical isomers, pharmaceutically acceptable salts, hydrates or solvates thereof, may be employed in an amount of from about 0.1 to about 99.5 wt %, and preferably in an amount of from about 0.5 wt % to about 95 wt %.

The pharmaceutical composition comprising one of the compounds of Chemical Formulas 1 to 3 as an active ingredient may be administered orally, rectally, intravenously, intraarterially, intraperitoneally, intramuscularly, intrathoracically, transdermally, topically, intraocularly, or intradermally.

In accordance with another aspect thereof, the present invention provides a health food for the prevention or improvement of metabolic bone diseases, comprising a spinasterol glucoside derivative represented by Chemical Formula 1, or an optical isomer, a pharmaceutically acceptable salt, a hydrate or a solvate thereof.

In this context, the spinasterol glucoside derivative of the present invention, or an optical isomer, a pharmaceutically acceptable salt, a hydrate or a solvate thereof may be added as it is, or may be used together with another food or a food ingredient.

No particular limitations are imparted to the kind of the health food to which the spinasterol glucoside derivative of the present invention can be added. Examples of such a health food include meats, sausages, breads, chocolates, candies, snacks, confectionery, pizzas, ramen noodles, other noodles, gums, dairy products such as ice-creams, various soups, beverages, teas, drinks, alcoholic beverages, and vitamin complexes. All typically accepted health foods may contain the active ingredient according to the present invention.

In accordance with a further aspect thereof, the present invention addresses a method for treating a metabolic bone disease, using the spinasterol glucoside derivative of the present invention or an optical isomer, a pharmaceutically acceptable salt, a hydrate or a solvate thereof.

The method may be a preventive or palliative therapy. The method comprises administering a therapeutically effective amount of the spinasterol glucoside derivative of the present invention or an optical isomer, a pharmaceutically acceptable salt, a hydrate or a solvate thereof to a subject in need thereof. Preferably, the method is applied to humans.

Also, contemplated in accordance with a still further aspect of the present invention is the use of the spinasterol glucoside derivative of the present invention, or an optical isomer, a pharmaceutically acceptable salt, a hydrate or a solvate thereof in the treatment of a metabolic bone disease.

Advantageous Effects

As described hitherto, the spinasterol glucoside derivatives of the present invention, or optical isomers, pharmaceutically acceptable salts thereof, hydrates or solvates thereof are suppressive of weight loss, inflammation, edema, and stiffness of muscles and tendons, and regenerate the cartilage at worn joints Therefore, the spinasterol glucoside derivatives of the present invention, or optical isomers, pharmaceutically acceptable salts thereof, hydrates or solvates thereof can be effectively applied to the prophylaxis and therapy of metabolic bone diseases.

MODE FOR INVENTION

Figure 1:
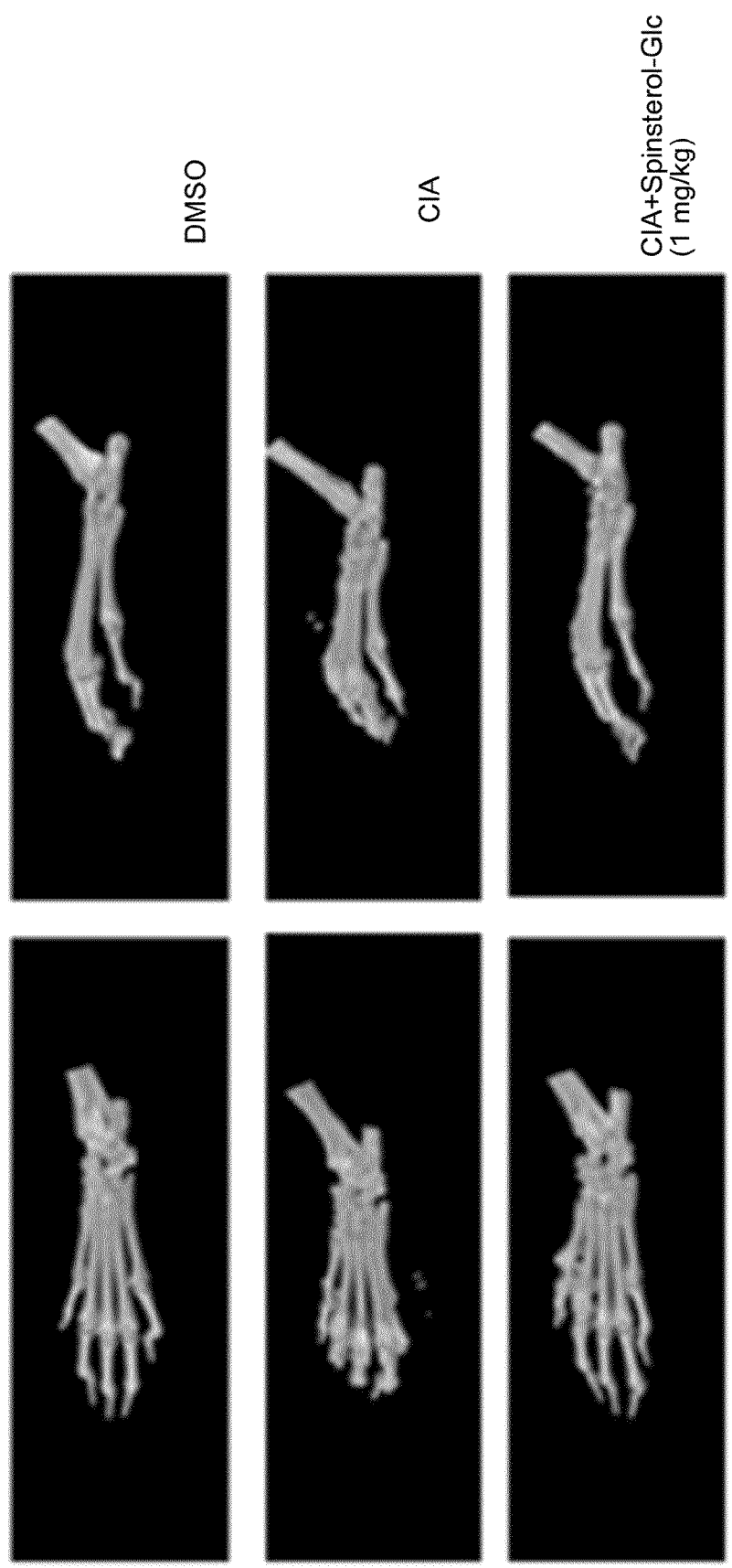
FIG. 1 shows the therapeutic effect of the spinasterol glucoside derivative on arthritis

A better understanding of the present invention may be obtained through the following examples which are set forth to illustrate, but are not to be construed as limiting the present invention.

Preparation Example

Preparation of Spinasterol Glucoside Derivative

1. Separation of Glucoside Compound from Extract of Leaves of *Stewartia koreana*

In 80% methanol (90 L), 8.5 kg of leaves of *Stewartia koreana* were immersed for 24 hrs, followed by filtration through a G3 glass filter. Extraction from the residue was repeated again with the same solvent (90 L). The filtrates thus obtained were pooled (180 L) and concentrated at 35° C. in a vacuum to afford a methanol extract (663 g).

The methanol extract (663 g) was partitioned with water (2 L) and ethyl acetate (2 L), and concentrated at a reduced pressured to give a water fraction (608 g) and an ethyl acetate fraction (52 g). This ethyl acetate fraction (52 g) was subjected to silica gel absorption column chromatography using a chloroform-methanol solvent (20:1~1:1, v/v) as an eluent, with TLC (thin-layer chromatography) monitoring of the eluates. The treatment of the crude extract fractions with sulfuric acid visualized fractions of high and low polarities, indicating the presence of many effective compounds. For this, the chromatography was carried out using a gradient of chloroform-methanol mixture from 20:1 to 1:1. The eluates were obtained in an amount of 1 liter in each of 18 glass containers.

Similar fractions were grouped according to their TLC profiles and UV absorbance profile (280 nm). A small amount (1 g) of each of the fractions was diluted in methanol, and measured for absorbance at 280 nm. For TLC, the fractions were run on a silica thin layer using a mixture of chloroform-methanol (10:1, v/v) as a developing solvent, with UV detection through a filter (280 nm). Sequentially eluted UV absorption fractions I (3-4), II (7-8), III (10-11), and IV (15-16) were collected and concentrated at a reduced pressure. Fractions I (3-4), II (7-8), III (10-11), and IV (15-16) were purified by silica gel absorption column chromatography using a gradient of chloroform-methanol mixtures from 10:1 (V/V) to 1:1 (V/V). Eluates were obtained in an amount of 1 liter in each of 16 glass containers.

A small amount (1 g) of each fraction was diluted in methanol and measured for absorbance at 280 nm. TLC was performed on a silica thin layer using a mixture of chloroform-methanol (5:1, V/V) as a developing solvent.

Nitrite activity was measured with UV light filters (254/365 nm) to detect active fractions. A substance responsible for nitrite activity was obtained (512 mg).

2. Structural Determination of Compound I by Instrumental Analysis.

The substance of 1 was obtained as a white powder with m. p. 279-284° C.; $[\alpha]D20$ $-12.59°$ (c=0.07, $C_5H_5N$); its mass was found to be $[M+Na]^+$ m/z 574.83 as measured by a pos. mass spectrometer FAB-MS (Jeo Ltd., JMS-HX/HX110A). In addition, $^1$H-NMR (pyridine-d5, 500 MHz) was measured as follows: δ 5.17 (2H, d, J=7.5 Hz, H-22), 5.06 (1H, m, H-23), 5.04 (1H, d, J=7.5 Hz, H-1'), 3.96-4.49 (5H, m, H-2', H-6'), 1.06 (3H, d, J=6.5 Hz, H-21), 0.89 (3H, d, J=6.0 Hz, H-26), 0.85-0.89 (6H, m, H-27, H-29), 0.72 (3H, s, H-19), 0.58 (3H, s, H-18). After TLC development, it appeared dark purple upon visualization with 10% sulfuric acid, and measured to be 280° C. in m. p. and 574 in EI/MS molecular weight.

On $^1$H-NMR spectra, two singlet methyl groups were read at δH 0.58 (3H) and 0.72 (3H), three methyl group signals at δH 0.85 (6H, m), 0.89 (3H, d, J=6.0 Hz), and 1.06 (3H, d, J=6.4 Hz), trans vicinal olefinic proton signals at δH 5.06 (1H, dd, J=16.0, 8.8 Hz) and 5.17 (1H, dd, J=16.0, 8.8 Hz), and an olefinic proton signal at δH 5.17 (1H, m). In addition, an anomeric proton was detected at δH 5.04 (1H, d, J=7.2 Hz). Therefore, the substance was inferred to be in the form of a glycoside.

A $^{13}$C-NMR spectrum allowed the inference of a structure having a total of 35 carbon atoms, reading an anomeric carbon signal at δC 102.32 and olefinic carbon signals at δC 117.89, 129.65, 138.69, and 139.60. In full consideration of these spectrometric data, the substance was determined to be spinasterol. The glycoside moiety was identified as D-glycopyranose by the chemical shift and analyzed to have a β-linkage coupling from a coupling constant of 7.2 Hz for the anomeric proton. In addition, 2D-NMR such as gHSQC or gHMBC revealed the linkage site of the glucoside moiety. Taken together, the data demonstrated that the substance was 3-o-β-D-glucopyranosyl-spinasterol represented by Chemical Formula 1.

Example 1

Prophylactic and Therapeutic Effect of the Spinasterol Glucoside Derivative on Arthritis The spinasterol glucoside derivative of the present invention was assayed in vivo for preventive activity against arthritis using animal models. For this, collagen was employed to induce arthritis in DBA1/J mice which were then treated with the spinasterol glucoside derivative of Chemical Formula 3, and tested.

An emulsion was formed by dissolving 2 mg/ml CII (type II collagen; Chondrex, Seattle, Wash.) at 4° C. in 50 mM acetic acid, and then by mixture with an equal volume of CFA containing 2 mg/ml *Mycobacterium tuberculosis*. Mice were injected intravenously at the tail with a total of 150 μl of the emulsion, followed by a second injection with an emulsion of CII in an indirect fluorescent antibody (IFA) as a booster 14 days after the first immunization. For 28 days after the immunization, the mice were challenged with PBS (120 μl) or 3-o-β-D-glucopyranosyl-spinasterol (10 μM/kg of weight, 100~120 μl) three times a week. 42 days later, the results were observed. The clinical severity of arthritis was determined by degrees of paw swelling. This was verified by micro-CT morphometry.

The results are shown in FIG. 1.

As can be seen in FIG. 1, collagen-induced arthritis was distinct in the positive control (collagen type II, CIA) which was found to have a decrease in weight, compared to the negative control (DMSO), and have edema. In contrast, the test group treated with the spinasterol glucoside derivative of Chemical Formula 3 (CIA+Spinsterol-Glc) was reduced in the degree of collagen-induced arthritis, compared to the positive control, and showed regeneration of cartilage at the worn joint.

From the results, it was apparent that the spinasterol glucoside derivatives of Chemical Formulas 1 to 3 exerted prophylactic and therapeutic effects on arthritis.

Example 2

Regenerative Effect of the Spinasterol Glucoside Derivatives on Cartilage

The cartilage regeneration activity of spinasterol glucoside derivatives were evaluated in osteoblast defected (OD) models which were widely used in study on the regeneration of degenerative articular cartilage. The cartilage of SD rats, at least 9 weeks of age, was destroyed by a 5 μm drill, followed by suturing the muscle and lipid tissues so as to allow them to go about normal daily life. Then, 3-o-β-D-glucopyranosyl-spinasterol dissolved in distilled water was orally administered at a dose of 1 mg/kg once every two days for 4 weeks. Afterwards, the animals were sacrificed, and opened around the knee to take articular cartilage tissues, followed by decalcification for 4 weeks. The cartilage tissues thus softened were paraffinized, and dyed with Safran O solution to visualize the regeneration of the cartilage.

Figure 2:
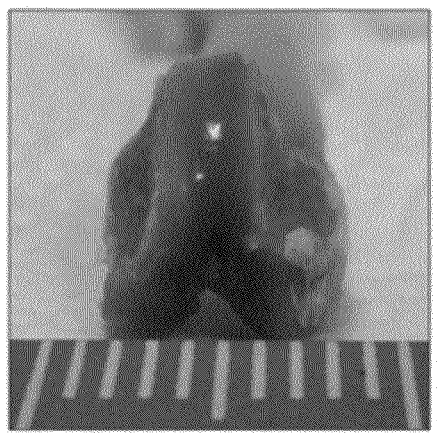
FIG. 2 shows the therapeutic effect of the spinasterol glucoside derivative on the regeneration of the cartilage.
Figure 2:
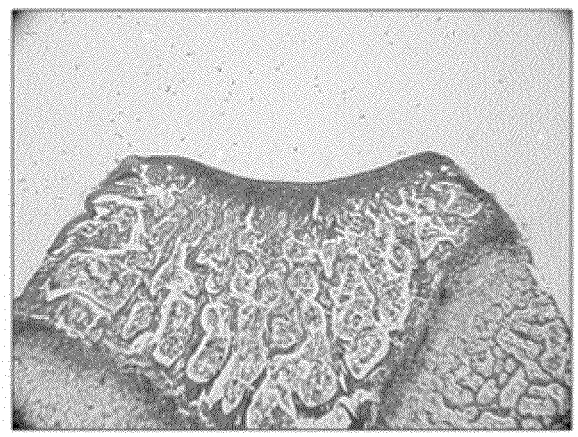
Figure 2:
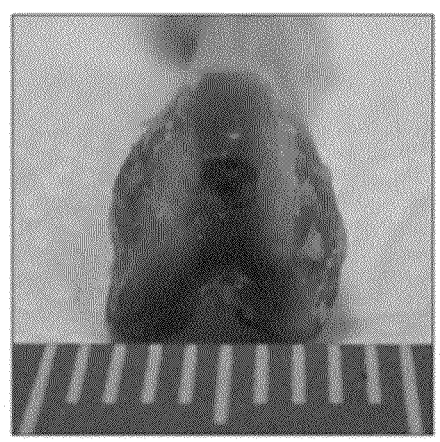
Figure 2:
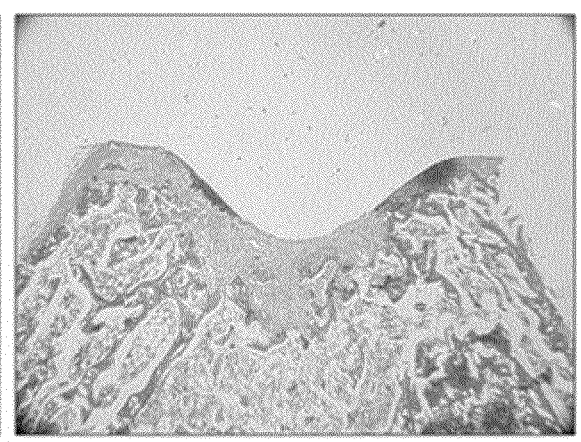
Figure 2:
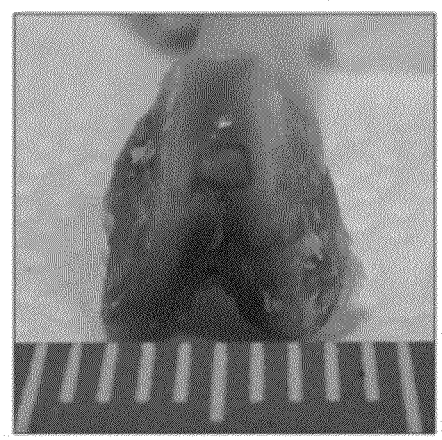
Figure 2:
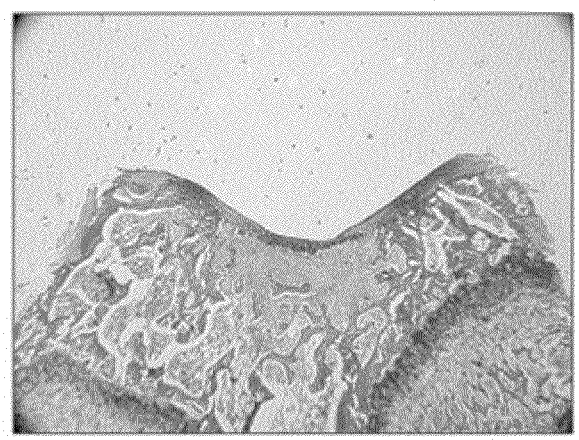

The results are given in FIG. 2.

As can be seen in FIG. 2, significant regeneration of cartilage tissues was found in the spinasterol glucoside derivative-treated group (c), compared to the control (b).

When treated with the spinasterol glucoside derivative, the DO models exhibited greatly increased levels of chondrocytes, mast cells, and mucin, demonstrating the regenerative effect of the spinasterol glucoside derivative on the cartilage.

The invention claimed is:

1. A method for treating metabolic bone disease in a patient comprising administering to the patient a composition comprising an effective amount of a spinasterol glucoside derivative represented by the following Chemical Formula 2, or an optical isomer, a pharmaceutically acceptable salt, a hydrate or a solvate thereof:

[Chemical Formula 2]

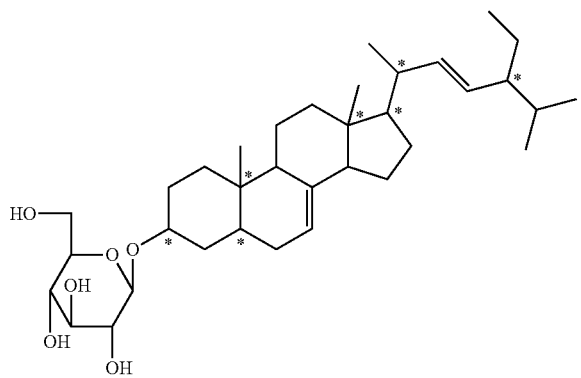

2. The method of claim 1, wherein the spinasterol glucoside derivative represented by Chemical Formula 2 is 3-O-β-D-glucopyranosyl spinasterol represented by the following Chemical Formula 3:

[Chemical Formula 3]

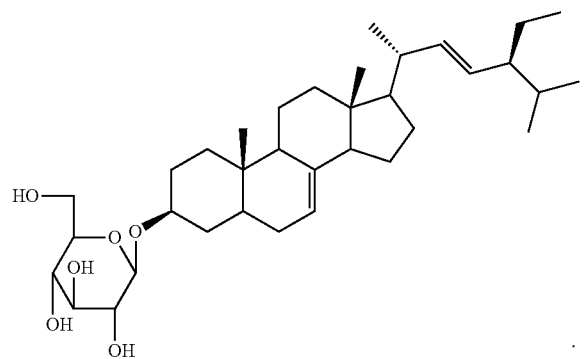

3. The method of claim 1, wherein the spinasterol glucoside derivative is separated from *Stewartia koreana*.

4. The method of claim 2, wherein the spinasterol glucoside derivative is separated from *Stewartia koreana*.

5. The method of claim 1, wherein the metabolic bone disease is osteoporosis, osteomalacia, osteopenia, bone atrophy, fibrous dysplasia, Paget's disease, hypercalcemia, cancer-related bone resorption, osteolysis, osteoarthritis, or rheumatoid arthritis.

6. The method of claim 2, wherein the metabolic bone disease is osteoporosis, osteomalacia, osteopenia, bone atrophy, fibrous dysplasia, Paget's disease, hypercalcemia, cancer-related bone resorption, osteolysis, osteoarthritis, or rheumatoid arthritis.

* * * * *